United States Patent
Tang et al.

(10) Patent No.: US 11,186,607 B1
(45) Date of Patent: Nov. 30, 2021

(54) PLEUROMUTILIN URSODEOXYCHOLIC ACID ESTER WITH ANTIBACTERIAL ACTIVITY AND A METHOD OF PREPARING THE SAME

(71) Applicants: Yonghong Tang, Xi'an (CN); Bin Tian, Xi'an (CN); Lei Tian, Xi'an (CN); Yanjun Li, Xi'an (CN); Qiao Zeng, Xi'an (CN); Dan Yang, Xi'an (CN); Liang Xin, Xi'an (CN); Jingyi Li, Xi'an (CN); Qianqian Zhao, Xi'an (CN); Minghui Chang, Xi'an (CN); Huafeng Qi, Xi'an (CN); Zhuanmei Yuan, Xi'an (CN); Wenbo Yao, Xi'an (CN); Guaiping Qiao, Xi'an (CN); Juan Li, Xi'an (CN); Nan Hui, Xi'an (CN); Han Li, Xi'an (CN)

(72) Inventors: Yonghong Tang, Xi'an (CN); Bin Tian, Xi'an (CN); Lei Tian, Xi'an (CN); Yanjun Li, Xi'an (CN); Qiao Zeng, Xi'an (CN); Dan Yang, Xi'an (CN); Liang Xin, Xi'an (CN); Jingyi Li, Xi'an (CN); Qianqian Zhao, Xi'an (CN); Minghui Chang, Xi'an (CN); Huafeng Qi, Xi'an (CN); Zhuanmei Yuan, Xi'an (CN); Wenbo Yao, Xi'an (CN); Guaiping Qiao, Xi'an (CN); Juan Li, Xi'an (CN); Nan Hui, Xi'an (CN); Han Li, Xi'an (CN)

(73) Assignee: Xi'an Taikomed Pharmaceutical Technology Co., Ltd., Xi'an (CN)

( * ) Notice: Subject to any disclaimer, the term of this patent is extended or adjusted under 35 U.S.C. 154(b) by 0 days.

(21) Appl. No.: 17/134,241

(22) Filed: Dec. 25, 2020

(51) Int. Cl.
*C07J 9/00* (2006.01)

(52) U.S. Cl.
CPC .................................... *C07J 9/005* (2013.01)

(58) Field of Classification Search
CPC ....................................................... C07J 9/005
See application file for complete search history.

*Primary Examiner* — Barbara P Badio

(57) ABSTRACT

A compound with antibacterial activity having the following formula (I):

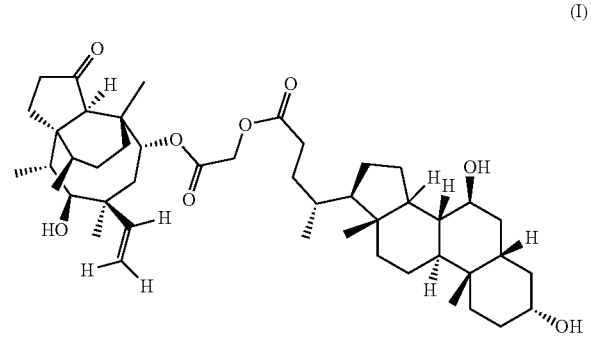

is disclosed. A method of preparing the compound of formula (I) is also disclosed.

14 Claims, 2 Drawing Sheets

PLEUROMUTILIN URSODEOXYCHOLIC ACID ESTER WITH ANTIBACTERIAL ACTIVITY AND A METHOD OF PREPARING THE SAME

FIELD OF THE INVENTION

The present invention relates to the field of medicinal chemistry, and in particular, to a pleuromulin ursodeoxycholic acid ester with antibacterial activity and a method of preparing the same.

BACKGROUND OF THE INVENTION

In recent years, various types of drug-resistant bacteria have developed rapidly, which makes the drug resistance rate and infectious problems more serious. Multidrug-resistant bacteria infections (MDRB) are resistant to three or more types of antibacterial drugs. Common MDRBs include *Escherichia coli, Staphylococcus aureus, Acinetobacter baumannii, Pseudomonas aeruginosa*, and multidrug-resistant *Mycobacterium tuberculosis*. At present, multi-drug-resistant bacteria are an important source of infection, and the difficulty of controlling infection with antibacterial drugs is increasing. Therefore, it is urgent to solve the problem of bacterial resistance.

Pleuromulin is a tricyclic diterpenoid veterinary antibiotic produced by the submerged fermentation of the fungus *Clitopilus pinsitus* of the genus *Stropharia*, which is composed of a 5-6-8 three-membered ring skeleton containing 8 chiral carbon atoms and a glycolate side chain. It is the precursor of synthetic animal-specific antibiotic tiamulin. It has strong antibacterial activity against gram-positive bacteria and mycoplasma. Pleuromutilin drugs act on peptidyl transferase center (PTC) of bacterial ribosomes to interfere with tRNA and P-site and A-Site binding, thus inhibiting the protein synthesis of the bacterial.

Ursodeoxycholic acid (also known as ursodiol) is a natural bile acid separated from bear bile. It is an epimer of chenodeoxycholic acid. Its stone-dissolving effect and curative effect are similar to chenodeoxycholic acid, but the course of treatment short, small dose. It is suitable for the treatment of cholesterol stones, hyperlipidemia, disorders of bile secretion, primary biliary cirrhosis, chronic hepatitis, bile reflux gastritis, and prevention of acute rejection and reaction of liver transplantation.

In the present invention, pleuromulin is modified by ursodeoxycholic acid structure to obtain a novel pleuromulin ursodeoxycholic acid ester. Preliminary in vitro antibacterial activity experiment shows that the compound has excellent antibacterial activity and anti-drug-resistant bacteria activity.

SUMMARY OF THE INVENTION

In one embodiment, the present invention provides a compound having the following formula (I):

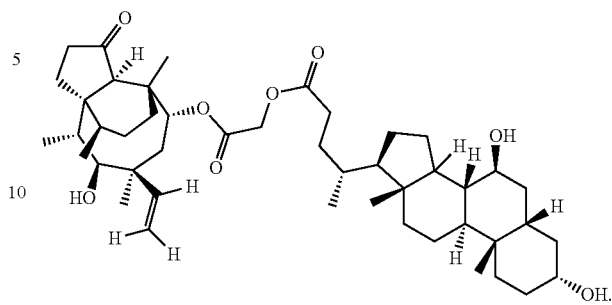

In another embodiment, the present invention provides a method of preparing the compound of formula (I). The method includes: reacting a compound of formula (II) with a compound of formula (III) to obtain the compound of formula (I):

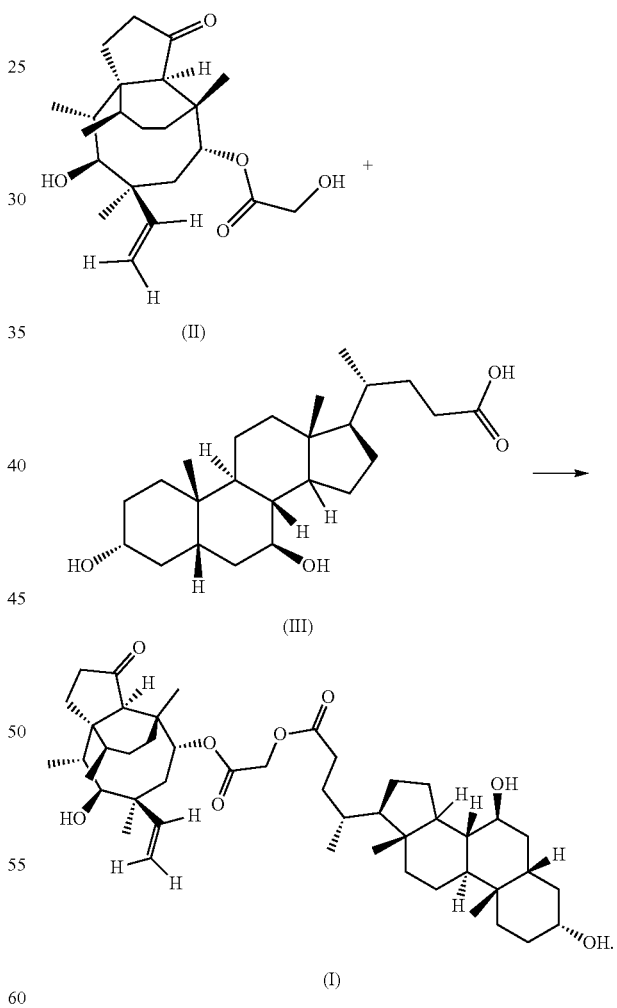

In another embodiment, the reaction of the compound of formula (II) with the compound of formula (III) comprises the following steps: placing the compound of formula (III) in a reactor; adding an organic solvent and coupling agent DCC (N,N'-dicyclohexylcarbodiimide) under nitrogen atmosphere to obtain a reaction mixture; stirring the reaction mixture at 0° C. for five minutes; adding a catalytic amount of 4-DMAP (4-dimethylaminopyridine) and the compound of formula (II) to the reaction mixture; heating the reaction mixture at 20-60° C. for 8-12 hours; and extracting the reaction mixture with ethyl acetate to obtain a crude product; and purifying the crude product on a silica gel fresh chromatography column with dichloromethane and methanol as an eluent to obtain the compound of formula (I).

In another embodiment, the organic solvent is toluene, methylene chloride or DMF (dimethylformamide).

In another embodiment, the organic solvent is methylene chloride.

In another embodiment, a molar ratio of the compound of formula (II) and the compound of formula (III) is 1:1.1.

In another embodiment, the reaction mixture is heated at 25° C.

In another embodiment, the reaction mixture is heated for 10 hours.

In another embodiment, the eluent is dichloromethane:methanol=15:1.

In another embodiment, the reaction of the compound of formula (II) with the compound of formula (III) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 20-40° C. for 4-8 hours; placing the reaction mixture in a separating funnel to separate a crude product; purifying the crude product by recrystallization in methanol to obtain the compound of formula (I); and recycling the ionic liquid.

In another embodiment, the ionic liquid is 1-ethyl-3-methylimidazolium tetrachloroferrate, 1-hexyl-3-methylimidazolium tetrafluoroborate or 1-octyl-3-methylimidazolium hexafluorophosphate ($C_{12}H_{23}F_6N_2P$).

In another embodiment, the ionic liquid is 1 octyl-3-methylimidazolium hexafluorophosphate.

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 30° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
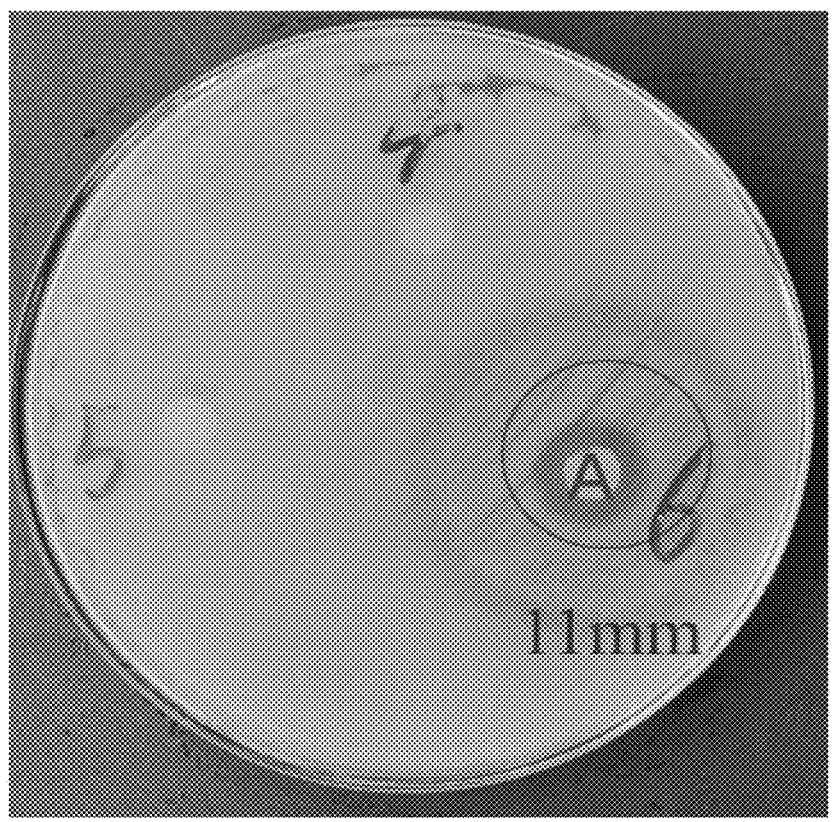
FIG. 1 shows the in vitro antibacterial activity of the pleuromulin ursodeoxycholic acid ester against drug-resistant bacteria MRSA 171.

Reference will now be made in detail to embodiments of the present invention, example of which is illustrated in the accompanying drawings. The following examples illustrate the present invention, but the present invention is not limited to the following examples.

Example 1

Preparation of the pleuromulin ursodeoxycholic acid ester ((4R)-2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl 4-((3R,5 S,7 S, 8R,9 S, 10 S,13R,17R)-3,7-dihydroxy-10,13-dimethylhexadecahydro-1H-cyclopenta[a]phenanthren-17-yl)pentanoate)

In a 100 mL three-neck flask, 215.9 mg (0.55 mmol) of ursodeoxycholic acid and 103.2 mg (0.50 mmol) of DCC (N,N'-dicyclohexylcarbodiimide) were dissolved in 20 mL dichloromethane, and stirred at 0° C. for five minutes. After adding 6.1 mg (0.05 mmol) of 4-DMAP (4-(dimethylamino) pyridine) to the reaction mixture, 189.1 mg (0.50 mmol) of pleuromulin was added slowly under nitrogen atmosphere. The ice bath device was removed. The reaction mixture was stirred at 25° C. for 10 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:1, and the eluent containing the product was concentrated under reduced pressure and dried to obtain 284.5 mg of the pleuromulin ursodeoxycholic acid ester, a total yield of 75.6%.

$^1$H-NMR (400 MHz, chloroform-d) δ (ppm): 6.51 (1H, t), 5.84 (1H, d), 5.34 (2H, s), 5.23 (1H, d), 4.62 (1H, t), 4.48 (1H, s), 3.77-3.62 (3H, m), 3.59 (1H, t), 3.41 (1H, t), 2.39 (2H, m), 2.30 (1H, s), 2.14 (4H, t), 1.99-1.27 (28H, m), 1.20-1.06 (7H, m), 0.99-0.94 (9H, s), 0.88-0.73 (9H, s); $^{13}$C-NMR (400 MHz, chloroform-d) δ (ppm): 216.9, 173.3, 166.8, 138.8, 117.3, 77.2, 74.6, 71.4, 71.3, 69.6, 58.1, 54.9, 44.0, 37.3, 36.0, 34.4, 30.7, 26.9, 23.4, 16.5, 12.1.

Example 2

Preparation of the Pleuromulin Ursodeoxycholic Acid Ester

In a 100 mL three-neck flask, 215.9 mg (0.55 mmol) of ursodeoxycholic acid and 103.2 mg (0.50 mmol) of DCC were dissolved in 20 mL dichloromethane, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 30° C. for 9 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:2, and the eluent containing the product was concentrated under reduced pressure and dried to obtain 272.0 mg of the pleuromulin ursodeoxycholic acid ester, a total yield of 72.3%.

Example 3

Preparation of the Pleuromulin Ursodeoxycholic Acid Ester

In a 100 mL three-neck flask, 215.9 mg (0.55 mmol) of ursodeoxycholic acid and 103.2 mg (0.50 mmol) of DCC were dissolved in 20 mL dichloromethane, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 40° C. for 8 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:1, and the eluent containing the product was concentrated under reduced pressure and dried to obtain 263.8 mg of the pleuromulin ursodeoxycholic acid ester, a total yield of 70.1%.

Example 4

Preparation of the Pleuromulin Ursodeoxycholic Acid Ester

In a 100 mL three-neck flask, 235.5 mg (0.60 mmol) of ursodeoxycholic acid and 103.2 mg (0.50 mmol) of DCC were dissolved in 20 mL dichloromethane, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 35° C. for 8 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15: 2, and the eluent containing the product was concentrated under reduced pressure and dried to obtain 280.3 mg of the pleuromulin ursodeoxycholic acid ester, a total yield of 74.5%.

Example 5

Preparation of the Pleuromulin Ursodeoxycholic Acid Ester

In a 100 mL three-neck flask, 215.9 mg (0.55 mmol) of ursodeoxycholic acid and 103.2 mg (0.50 mmol) of DCC were dissolved in 20 mL dichloromethane, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 30° C. for 10 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:1, and the eluent containing the product was concentrated under reduced pressure and dried to obtain 258.9 mg of the pleuromulin ursodeoxycholic acid ester, a total yield of 68.8%.

Example 6

Preparation of the Pleuromulin Ursodeoxycholic Acid Ester

In a 100 mL three-neck flask, 215.9 mg (0.55 mmol) of ursodeoxycholic acid and 103.2 mg (0.50 mmol) of DCC were dissolved in 20 mL toluene, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 60° C. for 8 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:2, and the eluent containing the product was concentrated under reduced pressure and dried to obtain 243.4 mg of the pleuromulin ursodeoxycholic acid ester, a total yield of 64.7%.

Example 7

Preparation of the Pleuromulin Ursodeoxycholic Acid Ester

In a 100 mL three-neck flask, 235.5 mg (0.60 mmol) of ursodeoxycholic acid and 103.2 mg (0.50 mmol) of DCC were dissolved in 20 mL toluene, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 50° C. for 9 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:2, and the eluent containing the product was concentrated under reduced pressure and dried to obtain 234.4 mg of the pleuromulin ursodeoxycholic acid ester, a total yield of 62.3%.

Example 8

Preparation of the Pleuromulin Ursodeoxycholic Acid Ester

In a 100 mL three-neck flask, 255.2 mg (0.65 mmol) of ursodeoxycholic acid and 103.2 mg (0.50 mmol) of DCC were dissolved in 20 mL toluene, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 50° C. for 10 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:1, and the eluent containing the product was concentrated under reduced pressure and dried to obtain 247.6 mg of the pleuromulin ursodeoxycholic acid ester, a total yield of 65.8%.

Example 9

Preparation of the Pleuromulin Ursodeoxycholic Acid Ester

In a 100 mL three-neck flask, 235.5 mg (0.60 mmol) of ursodeoxycholic acid and 103.2 mg (0.50 mmol) of DCC were dissolved in 20 mL toluene, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 40° C. for 11 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:2, and the eluent containing the product was concentrated under reduced pressure and dried to obtain 240.1 mg of the pleuromulin ursodeoxycholic acid ester, a total yield of 63.8%.

Example 10

Preparation of the Pleuromulin Ursodeoxycholic Acid Ester

In a 100 mL three-neck flask, 215.9 mg (0.55 mmol) of ursodeoxycholic acid and 103.2 mg (0.50 mmol) of DCC were dissolved in 20 mL toluene, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 25° C. for 12 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:1, and the eluent containing the product was concentrated under reduced pressure and dried to obtain 241.9 mg of the pleuromulin ursodeoxycholic acid ester, a total yield of 64.3%.

Example 11

Preparation of the Pleuromulin Ursodeoxycholic Acid Ester

In a 100 mL three-neck flask, 215.9 mg (0.55 mmol) of ursodeoxycholic acid and 103.2 mg (0.50 mmol) of DCC were dissolved in 20 mL DMF, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 30° C. for 12 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:1, and the eluent containing the product was concentrated under reduced pressure and dried to obtain 239.7 mg of the pleuromulin ursodeoxycholic acid ester, a total yield of 63.7%.

Example 12

Preparation of the Pleuromulin Ursodeoxycholic Acid Ester

In a 100 mL three-neck flask, 235.5 mg (0.60 mmol) of ursodeoxycholic acid and 103.2 mg (0.50 mmol) of DCC were dissolved in 20 mL DMF, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 50° C. for 11 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:2, and the eluent containing the product was concentrated under reduced pressure and dried to obtain 242.7 mg of the pleuromulin ursodeoxycholic acid ester, a total yield of 64.5%.

Example 13

Preparation of the Pleuromulin Ursodeoxycholic Acid Ester

In a 100 mL three-neck flask, 255.2 mg (0.65 mmol) of ursodeoxycholic acid and 103.2 mg (0.50 mmol) of DCC were dissolved in 20 mL DMF, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 60° C. for 10 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:2, and the eluent containing the product was concentrated under reduced pressure and dried to obtain 247.6 mg of the pleuromulin ursodeoxycholic acid ester, a total yield of 65.8%.

Example 14

Preparation of the Pleuromulin Ursodeoxycholic Acid Ester

In a 100 mL three-neck flask, 235.5 mg (0.60 mmol) of ursodeoxycholic acid and 103.2 mg (0.50 mmol) of DCC were dissolved in 20 mL DMF, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 60° C. for 8 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:1, and the eluent containing the product was concentrated under reduced pressure and dried to obtain 249.8 mg of the pleuromulin ursodeoxycholic acid ester, a total yield of 66.4%.

Example 15

Preparation of the Pleuromulin Ursodeoxycholic Acid Ester

In a 100 mL three-neck flask, 215.9 mg (0.55 mmol) of ursodeoxycholic acid and 103.2 mg (0.50 mmol) of DCC were dissolved in 20 mL DMF, and stirred at 0° C. for five minutes. After adding 6.1 mg (0.05 mmol) of 4-DMAP to the reaction mixture, 189.1 mg (0.50 mmol) of pleuromulin was added slowly under nitrogen atmosphere. The ice bath device was removed. The reaction mixture was stirred at 55° C. for 10 hours. Thin layer chromatography was used to track the reaction to completion, heating was stopped, and the protective device was removed. The reaction mixture was concentrated under reduced pressure and extracted with ethyl acetate. Ethyl acetate was washed with saturated ammonium chloride solution, and concentrated to obtain a crude product. The crude product was further purified by silica gel column chromatography, eluting with dichloromethane:methanol=15:1, and the eluent containing the product was concentrated under reduced pressure and dried to obtain 259.2 mg of the pleuromulin ursodeoxycholic acid ester, a total yield of 68.9%.

Example 16

Preparation of the Pleuromulin Ursodeoxycholic Acid Ester

In a 100 mL three-necked flask, 189.1 mg (0.50 mmol) of pleuromulin, 215.9 mg (0.55 mmol) ursodeoxycholic acid and 9.2 mg (0.005 mmol) silicomolybdic acid were dissolved in 30 mL of 1-octyl-3-methylimidazolium hexafluorophosphate under nitrogen atmosphere. After full dissolution, the reaction mixture was stirred at 30° C. for 6 hours. Thin layer chromatography was used to track the reaction to completion, heating was stopped, and the protective device was removed. The reaction mixture was allowed to separate into layers to obtain a crude product. 1-Octyl-3-methylimidazolium hexafluorophosphate was recovered and reused. The crude product was recrystallized with 20 mL methanol and dried to obtain 326.4 mg of the pleuromulin ursodeoxycholic acid ester, a total yield of 86.75%.

Example 17

Preparation of the Pleuromulin Ursodeoxycholic Acid Ester

In a 100 mL three-necked flask, 189.1 mg (0.50 mmol) of pleuromulin, 215.9 mg (0.55 mmol) ursodeoxycholic acid and 9.2 mg (0.005 mmol) silicomolybdic acid were dissolved in 30 mL of 1-ethyl-3-methylimidazolium tetrachloroferrate under nitrogen atmosphere. After full dissolution, the reaction mixture was stirred at 20° C. for 8 hours. Thin layer chromatography was used to track the reaction to completion, heating was stopped, and the protective device was removed. The reaction mixture was allowed to separate into layers to obtain a crude product. 1-Ethyl-3-methylimidazolium tetrachloroferrate was recycled and reused. The crude product was recrystallized with 20 mL methanol and dried to obtain 308.7 mg of the pleuromulin ursodeoxycholic acid ester, a total yield of 82.05%.

Example 18

Preparation of the Pleuromulin Ursodeoxycholic Acid Ester

In a 100 mL three-necked flask, 189.1 mg (0.50 mmol) of pleuromulin, 215.9 mg (0.55 mmol) ursodeoxycholic acid and 9.2 mg (0.005 mmol) silicomolybdic acid were dissolved in 30 mL of 1-hexyl-3-methylimidazolium tetrafluoroborate under nitrogen atmosphere. After full dissolution, the reaction mixture was stirred at 40° C. for 4 hours. Thin layer chromatography was used to track the reaction to completion, heating was stopped, and the protective device was removed. The reaction mixture was allowed to separate into layers to obtain a crude product. 1-Hexyl-3-methylimidazolium tetrafluoroborate was recycled and reused. The crude product was recrystallized with 20 mL methanol and dried to obtain 308.5 mg of the pleuromulin ursodeoxycholic acid ester, a total yield of 82.03%.

Example 19

Preparation of the Pleuromulin Ursodeoxycholic Acid Ester

In a 100 mL three-necked flask, 189.1 mg (0.50 mmol) of pleuromulin, 215.9 mg (0.55 mmol) ursodeoxycholic acid and 9.2 mg (0.005 mmol) silicomolybdic acid were dissolved in 30 mL of 1-octyl-3-methylimidazolium hexafluorophosphate under nitrogen atmosphere. After full dissolution, the reaction mixture was stirred at 30° C. for 6 hours. Thin layer chromatography was used to track the reaction to completion, heating was stopped, and the protective device was removed. The reaction mixture was allowed to separate into layers to obtain a crude product. 1-Octyl-3-methylimidazolium hexafluorophosphate was recycled and reused. The crude product was recrystallized with 20 mL methanol and dried to obtain 317.3 mg of the pleuromulin ursodeoxycholic acid ester, a total yield of 84.33%.

Example 20

Antibacterial Activity Test of the Pleuromulin Ursodeoxycholic Acid Ester

The antimicrobial efficacy was determined by a paper diffusion drug sensitivity test.

Experimental strains: multi-resistant *Staphylococcus aureus* 206, multi-resistant *Staphylococcus aureus* 575, multi-resistant *Staphylococcus aureus* 596. The experimental strains were provided by Huashan Hospital Affiliated to Fudan University (Institute of Antibiotic of Fudan University).

Drug sensitive paper: The drug sensitive paper was a special drug sensitive paper with a diameter of 6.35 mm and a water absorption of 0.02 mL. The control drug was vancomycin (30 μg/tablet); the test drugs were pleuromulin (30 μg/tablet), ursodeoxycholic acid (30 μg/tablet) and pleuromulin ursodeoxycholic acid ester (30 μg/tablet).

Reagents: LB agar medium, LA broth medium, 0.5% DMSO solution.

Equipment: Ultra-clean workbench, high-pressure sterilization pot, gas bath constant temperature shaking incubator.

Preparation of Bacterial Suspension:

The experimental strains were inoculated in non-selective medium and placed in air at 37° C. for 24 h. Pick a single colony that grows well and inoculate it into broth medium, incubate at 35° C.±2° C. for 6 hours, and use LA broth medium to calibrate the concentration of the bacterial solution to 0.5 Mie turbidimetric tube ($1.5 \times 10^8$ CFU/mL). A bacterial suspension is obtained.

Paper Diffusion Method Drug Sensitivity Test:

Weigh the LB dry powder, sterilize at 103.4 Kpa, 121.3° C. high-pressure steam for 15 min, and then put it in a 40° C.-50° C. water bath. Place a sterile empty plate (inner diameter 9 cm) on the surface of the ultra-clean table water table, shake and shake LB, and then pour the plate. The thickness of each plate is 3 mm to 4 mm. After the plate is cooled at room temperature, store it in the refrigerator at 2° C.-8° C. Use a sterile cotton swab to dip the bacterial solution, and evenly coat the surface of the LB plate 3 times. After inoculation of the bacterial suspension, the LB plate was dried at room temperature for 3 min to 5 min. Use sterile forceps to closely attach the antibacterial drug paper to the dish. Put the dish upside down and place it in a 37° C. incubator for 24 h. Observe the result and measure the diameter. Taking 0.5% DMSO solution as a negative control, the antibacterial activity is expressed by the diameter of the inhibition zone. The inhibition zone ≥17 mm, sensitive; the inhibition zone is 15 mm~16 mm, intermediary; the inhibition zone ≤14 mm, drug resistance.

Figure 2:
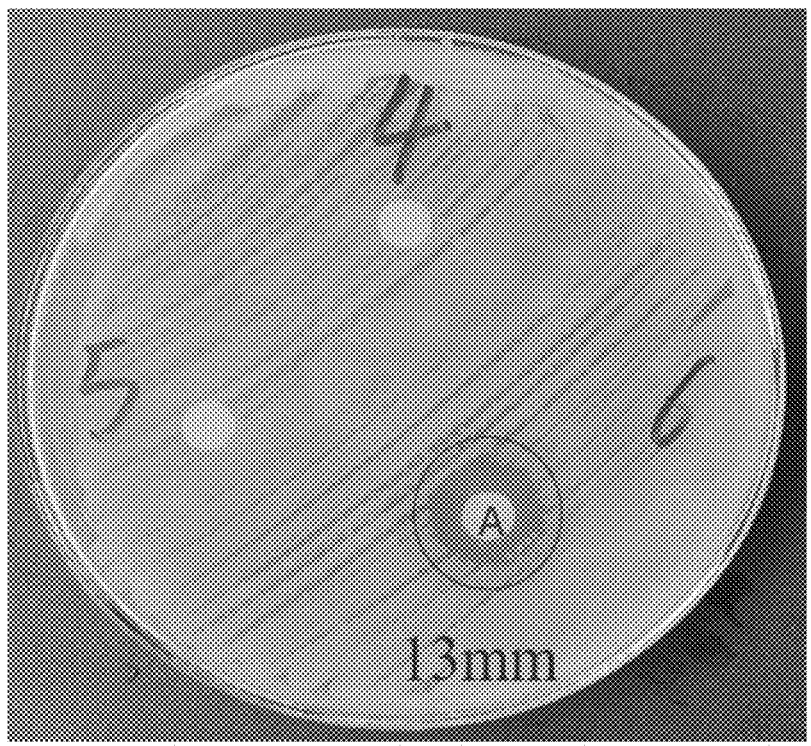
FIG. 2 shows the in vitro antibacterial activity of the pleuromulin ursodeoxycholic acid ester against drug-resistant bacteria MRSA 575.
Figure 3:
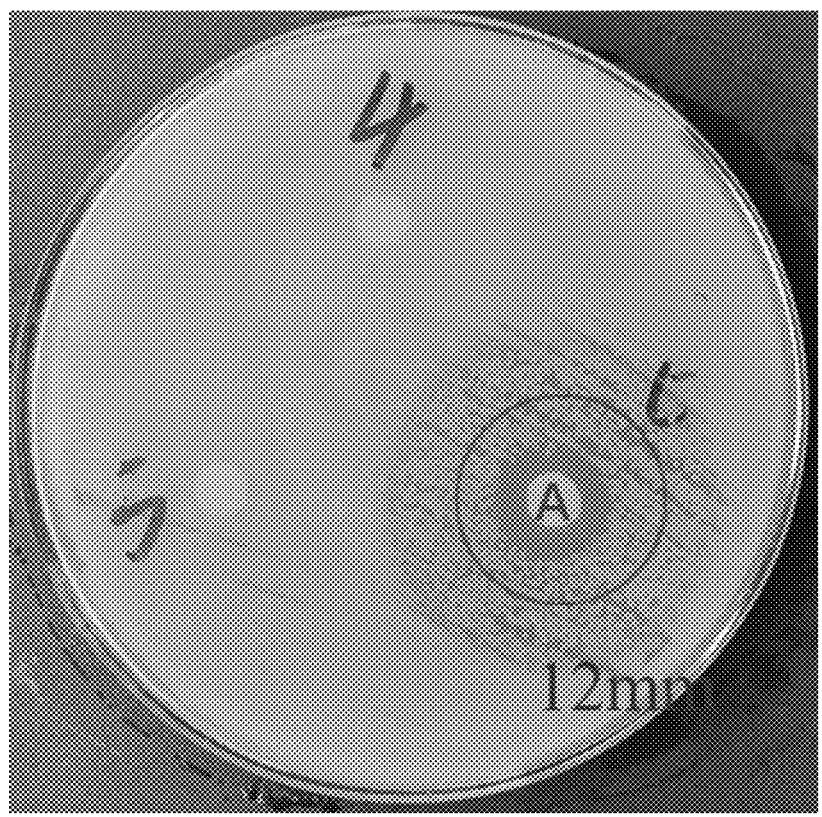
FIG. 3 shows the in vitro antibacterial activity of the pleuromulin ursodeoxycholic acid ester against drug-resistant bacteria MRSA 596.

In FIGS. 1, 2, and 3, the pleuromulin ursodeoxycholic acid ester is represented by the letter A. FIG. 1 shows the antibacterial effect of the pleuromulin ursodeoxycholic acid ester on MRSA-171. FIG. 2 shows the antibacterial effect of pleuromulin ursodeoxycholic acid ester on MRSA-575. FIG. 3 shows the antibacterial effect of pleuromulin ursodeoxycholic acid ester on MRSA-596. The results are shown in Table 1.

TABLE 1

Experimental results of the zone of inhibition

| Compound | Zone of inhibition/mm Strain | | |
|---|---|---|---|
| | MRSA-171 | MRSA-575 | MRSA-596 |
| 0.5% DMSO | 0 | 0 | 0 |
| Vancomycin | 17 | 17 | 23 |
| Pleuromulin | 0 | 0 | 0 |
| Ursodeoxycholic acid | 0 | 0 | 0 |
| Pleuromulin ursodeoxycholic acid ester | 11 | 13 | 12 |

The results in FIGS. 1-3 and Table 1 show that the starting raw materials pleuromutilin and ursodeoxycholic acid have no inhibitory effect on drug-resistant bacteria. The pleuromutilin ursodeoxycholic acid ester has strong inhibitory effects on multi-drug resistant *Staphylococcus aureus* 171, 575, 596, and the diameter of bacteriostatic zone against multidrug resistant *Staphylococcus aureus* 575 was up to 13 mm. In summary, the pleuromutilin ursodeoxycholic acid ester of the present invention can be used as an antibacterial drug candidate for multi-drug resistant *Staphylococcus aureus*, and further preclinical studies will be conducted.

What is claimed is:

1. A compound having the following formula (I):

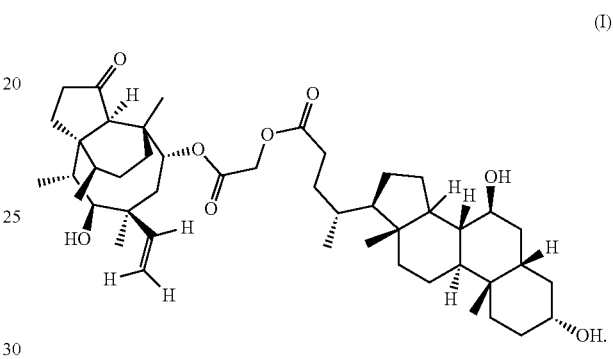

2. A method of preparing the compound of formula (I) of claim 1, comprising:

reacting a compound of formula (II) with a compound of formula (III) to obtain the compound of formula (I):

(II)

(III)

-continued

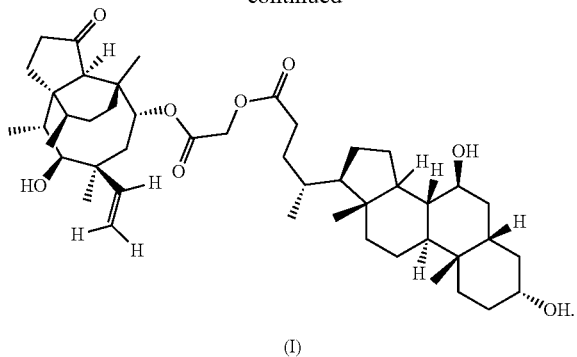

(I)

3. The method of claim 2, wherein the reaction of the compound of formula (II) with the compound of formula (III) comprises the following steps:
placing the compound of formula (III) in a reactor;
adding an organic solvent and coupling agent DCC (N,N'-dicyclohexylcarbodiimide) under nitrogen atmosphere to obtain a reaction mixture;
stirring the reaction mixture at 0° C. for five minutes;
adding a catalytic amount of 4-DMAP (4-dimethylaminopyridine) and the compound of formula (II) to the reaction mixture;
heating the reaction mixture at 20-60° C. for 8-12 hours; and
extracting the reaction mixture with ethyl acetate to obtain a crude product; and
purifying the crude product on a silica gel fresh chromatography column with dichloromethane and methanol as an eluent to obtain the compound of formula (I).

4. The method of claim 3, wherein the organic solvent is toluene, methylene chloride or DMF (dimethylformamide).

5. The method of claim 4, wherein the organic solvent is methylene chloride.

6. The method of claim 3, wherein a molar ratio of the compound of formula (II) and the compound of formula (III) is 1:1.1.

7. The method of claim 3, wherein the reaction mixture is heated at 25° C.

8. The method of claim 3, wherein the reaction mixture is heated for 10 hours.

9. The method of claim 3, wherein the eluent is dichloromethane:methanol=15:1.

10. The method of claim 2, wherein the reaction of the compound of formula (II) with the compound of formula (III) comprises the following steps:
placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 20-40° C. for 4-8 hours;
placing the reaction mixture in a separating funnel to separate a crude product;
purifying the crude product by recrystallization in methanol to obtain the compound of formula (I); and
recycling the ionic liquid.

11. The method of claim 10, wherein the ionic liquid is 1-ethyl-3-methylimidazolium tetrachloroferrate, 1-hexyl-3-methylimidazolium tetrafluoroborate or 1-octyl-3-methylimidazolium hexafluorophosphate ($C_{12}H_{23}F_6N_2P$).

12. The method of claim 11, wherein the ionic liquid is 1-octyl-3-methylimidazolium hexafluorophosphate.

13. The method of claim 10, wherein the compound of formula (II) and the compound (III) have a molar ratio of 1:1 to 1:1.3.

14. The method of claim 13, wherein the molar ratio of the compound of formula (II) and the compound of formula (III) is 1:1.1.

* * * * *